(12) United States Patent
Selig

(10) Patent No.: US 8,613,743 B2
(45) Date of Patent: Dec. 24, 2013

(54) HF SURGICAL TESTING DEVICE

(75) Inventor: Peter Selig, Hechingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 610 days.

(21) Appl. No.: 12/600,149

(22) PCT Filed: May 9, 2008

(86) PCT No.: PCT/EP2008/003770
§ 371 (c)(1),
(2), (4) Date: Nov. 13, 2009

(87) PCT Pub. No.: WO2008/138566
PCT Pub. Date: Nov. 20, 2008

(65) Prior Publication Data
US 2010/0312239 A1   Dec. 9, 2010

(30) Foreign Application Priority Data

May 14, 2007 (DE) .......................... 10 2007 022 548
Nov. 27, 2007 (DE) .......................... 10 2007 056 974

(51) Int. Cl.
*A61B 18/18* (2006.01)

(52) U.S. Cl.
USPC ............................................. 606/35; 606/34

(58) Field of Classification Search
USPC ...................................................... 606/34, 35
See application file for complete search history.

(56) References Cited

U.S. PATENT DOCUMENTS

| | | | |
|---|---|---|---|
| 4,745,918 A | 5/1988 | Feucht | |
| 4,754,757 A * | 7/1988 | Feucht | 606/35 |
| 4,788,977 A * | 12/1988 | Farin et al. | 606/35 |
| 5,087,257 A * | 2/1992 | Farin et al. | 606/35 |
| 5,441,520 A * | 8/1995 | Olsen et al. | 607/6 |
| 5,651,780 A * | 7/1997 | Jackson et al. | 606/1 |
| 5,971,981 A | 10/1999 | Hill et al. | |
| 6,125,298 A * | 9/2000 | Olson et al. | 607/5 |
| 6,560,485 B2 * | 5/2003 | Herleikson | 607/27 |
| 7,217,269 B2 * | 5/2007 | El-Galley et al. | 606/34 |
| 7,465,301 B2 * | 12/2008 | Bek et al. | 606/34 |

(Continued)

FOREIGN PATENT DOCUMENTS

| | | |
|---|---|---|
| DE | 43 39 049 A1 | 5/1995 |
| JP | 62-155841 A | 7/1987 |
| WO | WO 99/01074 | 1/1999 |

OTHER PUBLICATIONS

International Search Report, Aug. 20, 2008, PCT /EP2008/003770.

(Continued)

*Primary Examiner* — Linda Dvorak
*Assistant Examiner* — Jocelyn D Ram
(74) *Attorney, Agent, or Firm* — Dickstein Shapiro LLP

(57) ABSTRACT

A high-frequency surgical testing device for testing a neutral electrode during treatment, particularly during monopolar coagulation of biological tissue using a high-frequency current. The neutral electrode includes at least one first electrically conductive electrode segment having a first cable for connecting to a high-frequency generator, and a second electrically conductive electrode segment having a second cable for connecting to a high-frequency generator, the first and second electrode segments contacting the tissue. The test device includes an encoding element having a code for describing the neutral electrode and a measurement device for capturing the code describing the neutral electrode. The test device allows an identification of the neutral electrode to ensure safety.

16 Claims, 2 Drawing Sheets

(56) References Cited

U.S. PATENT DOCUMENTS

| | | | |
|---|---|---|---|
| 7,554,341 B2* | 6/2009 | Eisele | 324/682 |
| 7,722,603 B2* | 5/2010 | McPherson | 606/35 |
| 8,080,007 B2* | 12/2011 | Dunning et al. | 606/32 |
| 2001/0031962 A1* | 10/2001 | Eggleston | 606/35 |
| 2003/0014043 A1* | 1/2003 | Henry et al. | 606/34 |
| 2004/0054365 A1* | 3/2004 | Goble | 606/34 |
| 2005/0021022 A1* | 1/2005 | Sturm et al. | 606/35 |
| 2008/0071263 A1* | 3/2008 | Blaha | 606/35 |
| 2009/0198229 A1* | 8/2009 | Dunning | 606/35 |
| 2010/0217259 A1* | 8/2010 | Strauss | 606/38 |

OTHER PUBLICATIONS

Written Opinion for International Search Report, Aug. 20, 2008, PCT/EP2008/003770.

* cited by examiner

HF SURGICAL TESTING DEVICE

FIELD OF THE INVENTION

The disclosed embodiments relate to a high-frequency surgical testing device for testing a neutral electrode during treatment, particularly monopolar coagulation of biological tissue by means of a high-frequency current.

BACKGROUND

High-frequency surgery has been used for many years in both human and veterinary medicine in order to coagulate and/or cut biological tissue. With the aid of suitable electrosurgical instruments, high-frequency current is conducted through the tissue to be treated, so that said tissue changes due to protein coagulation and dehydration. In the process, the tissue contracts such that the vessels become closed and bleeding is stopped. A subsequent increase in the current density brings about explosive evaporation of the tissue fluid and tearing open of the cell membranes, so that the tissue is fully parted.

Both bipolar and monopolar techniques are used for the thermal treatment of biological tissue. In the case of monopolar arrangements, the high-frequency current fed from the high-frequency generator to the electrosurgical instrument is applied to the tissue to be treated via a 'different' electrode, wherein the current path runs through the body of a patient to an 'indifferent' neutral electrode and from there back to the high-frequency generator. A high current density per unit area is provided at the 'different' electrode for the treatment, whereas at the 'indifferent' electrode, the current density per unit area is significantly less compared with the 'different' electrode. This can be achieved with a suitably large area configuration of the neutral electrode. This arrangement ensures that no injuries, such as burns, occur in the tissue at the interface between the tissue and the neutral electrode.

In order to perform a coagulation, a high-frequency surgical apparatus is used which comprises an high-frequency surgical device with an high-frequency generator to create a high-frequency voltage or a high-frequency alternating current, as well as switching equipment and/or control and regulating equipment for activating or deactivating, or more generally for controlling the high-frequency generator.

For the safety of the patient, provision should be made, during a procedure, for constantly checking whether the neutral electrode is operating correctly and, for example, is properly placed on the patient. Any detachment of the electrode leads to a dangerous increase in the current density at the regions which still adhere, so that the injuries mentioned above could possibly occur. In order to ensure a high degree of safety for the patient, monitoring circuits are used which, for example, test the adhesion of the neutral electrode on the patient. Neutral electrode monitoring circuits of this type in a high-frequency surgical apparatus typically determine the transition resistance and/or the current distribution between the two conductive segments of the neutral electrode. Conclusions are often drawn concerning possible heating of the electrodes from these measured values. However, these conclusions are only relevant if electrode-specific parameters, such as area, geometry and structure of the electrodes are known. Particularly problematic in this context is the evaluation of very small neutral electrodes such as those sold for use with babies and small children. These can only be operated with a reduced high-frequency current strength since otherwise the heating can reach unacceptably high values. Also problematic herein is assessing neutral electrodes for their 'operating behavior'.

It is therefore an object of the disclosed embodiments to provide a high-frequency surgical testing device which not only enables this evaluation and assures a high level of safety both for the patient and the surgeon when using a neutral electrode and but also is as easy to use as possible.

SUMMARY

Disclosed embodiments include a high-frequency surgical testing device for testing a neutral electrode during treatment, in particular monopolar coagulation of biological tissue by means of a high-frequency current, wherein the neutral electrode comprises at least one first electrically conductive electrode segment which can be brought into contact with the tissue and has a first cable for connecting to a high-frequency generator and a second electrically conductive electrode segment which can be brought into contact with the tissue and has a second cable for connecting to the high-frequency generator and wherein the testing device comprises an encoding element with a coding characterizing the neutral electrode between the first and second electrode segments, and a measurement device which is configured so that the coding can be detected in order to identify the neutral electrode.

In the disclosed embodiments, electrode identification can be carried out with divided neutral electrodes, allowing the treatment process to be designed more readily plannable. Through identification of the neutral electrode, i.e. by identifying the type of the neutral electrode, the course of the treatment can be optimized and a high degree of safety for the patient can be assured. For example, depending on the identified neutral electrode, particular current and/or voltage values can be specifically set.

Preferably, the testing device or measurement device comprises a source for direct current or low frequency alternating current as a testing current, in order to detect the coding of the encoding element. Electrical and/or electronic decoding can be carried out without great difficulty. In the process, a property of the hydrogel used to fasten the neutral electrode to the patient is utilized. The hydrogel in question has a chemical composition such that it has very low electrical conductivity for direct currents and alternating currents of very low frequency (up to ca. 100 Hz), i.e. it has high ohmic resistance. If an encoding element is now installed on the divided neutral electrode between the two partial surfaces, said encoding element can be measured with the direct current signal or the alternating current signal of very low frequency. Since the gel has a high resistance in this condition, it is irrelevant whether the neutral electrode is placed on the patient, i.e. whether a low value parallel resistance through the tissue is present or not.

According to one disclosed embodiment, the testing device, or at least portions of the testing device, is/are arranged between the first cable and the second cable such that the test current can be conducted via the first and second cable. Since the test current—as distinct from the working current—is a direct current or a low frequency alternating current, it is possible to detect the characterizing coding without providing a special conductor for this purpose. The existing cable system therefore simultaneously serves as a cable system for the measurement device and thus for detecting the coding. An additional test line or measuring line is therefore not necessary. This means that a significant advantage with regard to compatibility results therefrom that, despite the extended functional scope of the neutral electrode identification, only the two existing neutral electrode connections are used for measuring. Thus the electrodes, the connecting cables and the plug connectors remain compatible with the components available on the market. No additional cables or electrical contacts are needed.

In another disclosed embodiment, the encoding element includes a resistor element having a resistance value which characterizes the neutral electrode, wherein the testing device is configured such that the resistance value can be detected to identify the neutral electrode. Encoding via a resistor element can be carried out easily and is also easily identified by means of the test current.

The resistor element is preferably configured as an ohmic resistor or a complex resistor with inductive behavior. The resistors used (encoding resistors) must have resistance values that are significantly smaller than the resistance of the gel at the measuring frequency. However, the values must be large enough such that no appreciable high-frequency currents can flow via the resistance between the two electrode segments. Typical values lie in the range of 1 k$\Omega$<$R_K$<100 k$\Omega$. For direct current and alternating current of low frequency, the relation $R_{Gel}$>$R_K$>$R_P$ applies.

In another disclosed embodiment, the resistor element is provided as a resistor film or resistor wire integrated into the neutral electrode. It is herein possible to equip even electrodes without fixed cables which are contacted via a suitable cable to a terminal with this functionality. The resistor element is therefore installed, for example, in the divided neutral electrode between the two electrode segments.

In the case of electrodes that are equipped with suitable cables, the encoding element or the resistor element, or possibly resistor elements, can be arranged between the first cable and the second cable. The application of a resistor, for example, to the cable segments, can be very easily realized.

Decoupling the test current from the (high-frequency) working current can be undertaken, for example, by connecting in an inductor as a filter element into the measuring system.

In another disclosed embodiment, the testing device or the measurement device comprises a voltage measurement device for measuring a voltage across the encoding element or resistor element (e.g. arising from the test current). The resistance value can therefore be easily determined for the respective neutral electrode. It is also possible to measure the coding or the resistance value by means of a current measurement device for measuring the direct current or the low-frequency current. This type of indirect measurement can be carried out without difficulty.

In another disclosed embodiment of the testing device, the testing device or at least parts of the testing device are configured to be integrated in the high-frequency generator to generate a high-frequency voltage. This means that the high-frequency generator is configured such that when the neutral electrode is plugged into the generator, an identification procedure can be performed, without a separate apparatus being necessary to do so. In other words, the testing device can be integrated in a high-frequency surgical apparatus.

In another disclosed embodiment, the testing device is configured such that it controls the high-frequency generator to the relevant setting, depending on the coding detected, for example, based on the resistance value detected. This means that all the values to be set at the high-frequency generator, such as current strength, would be automatically set depending on the neutral electrode that is identified. This is particularly advantageous when neutral electrodes are used which would cause burning of the patient upon exceeding a particular current strength. Therefore, a suitable current limitation could be automatically implemented, particularly with neutral electrodes for babies and small children.

It is also possible for a control device to be assigned to the testing device, the control device (which is possibly also integrated into the testing device) being configured to control the high-frequency generator to the setting thereof depending on the detected coding or the detected resistance value. A distinct control device could also be configured programmable for this purpose and could thus take over the control or regulation of the high-frequency generator.

It is also possible to carry out the relevant settings based on the detected resistance value by hand. As soon as the surgeon receives the feedback from the system concerning the detected neutral electrode, he can make the required settings, particularly on the high-frequency generator.

A storage device is preferably assigned to the testing device, in which the encodings, for example, the resistance values of resistor elements, of different neutral electrodes, can be stored as comparison values for neutral electrode identification. Thus, details concerning the neutral electrodes used can be output in simple manner which simplifies assignment for the user and enables planning of the progress of the intervention. The surgeon can therefore make suitable settings on the high-frequency generator which are adapted to the neutral electrode used.

Information concerning the neutral electrode identified can, quite generally, be output via a display on the high-frequency generator or on the high-frequency surgical apparatus. Sounds, light signals or the like can also be used for this purpose.

Preferably, the testing device is assigned to an input unit which is configured such that a user can, for example, input the comparative values into the storage device. Any other communication with the high-frequency surgical apparatus is also possible via the input unit, for example, a keyboard. The storage device can also be configured so that encodings that are not yet stored, or the values of any resistors of neutral electrodes, are detected and stored as soon as they are detected by the measurement device.

BRIEF DESCRIPTION OF THE DRAWINGS

The disclosed embodiments will now be described by reference to example embodiments which will be explained in greater detail with reference to the enclosed drawings.

DETAILED DESCRIPTION

In the following description, the same reference signs are used for the same and similarly acting parts.

Figure 1:
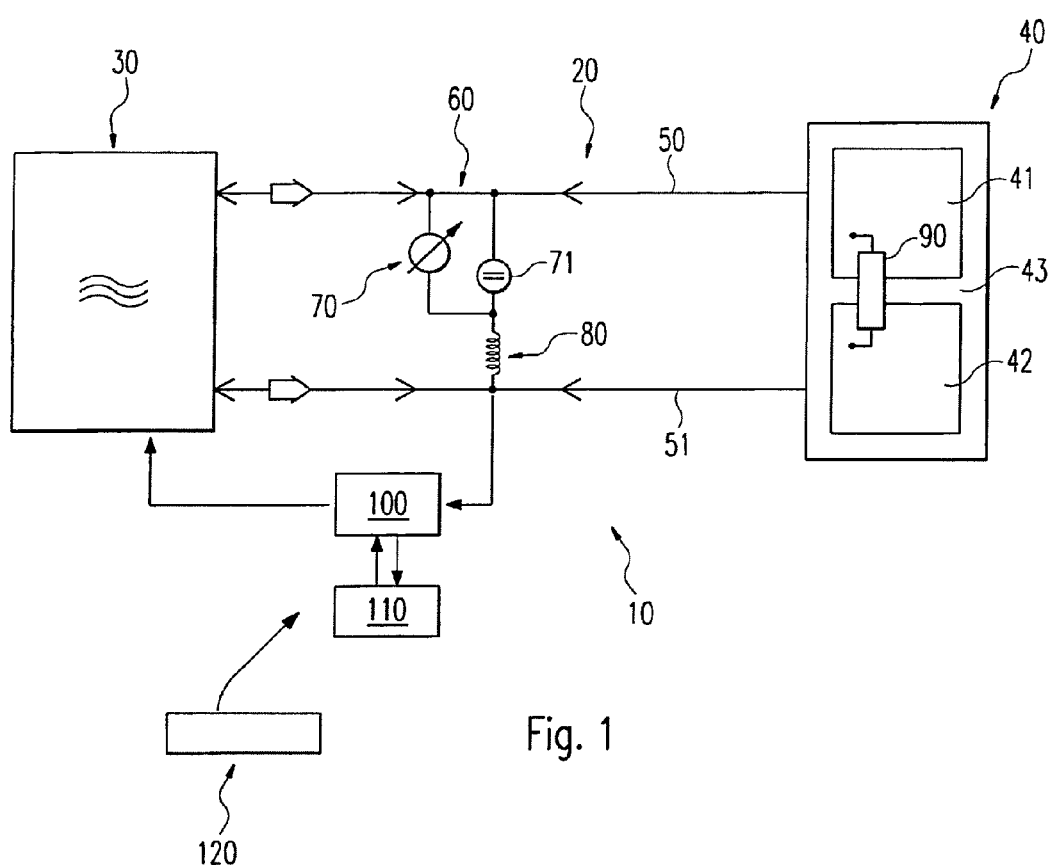
FIG. 1 illustrates a testing device according to a disclosed embodiment.

FIG. 1 illustrates one disclosed embodiment of a testing device 20. As shown in FIG. 1, a two-part neutral electrode 40 is connected to a high-frequency generator 30 of a high-frequency surgical apparatus 10, said high-frequency generator 30 supplying a high-frequency current. The neutral electrode 40 has a first electrically conductive electrode segment 41 and a second electrically conductive electrode segment 42, wherein the first electrode segment 41 is connected to the high-frequency generator 30 via a first cable 50 and the second electrode segment 42 is connected thereto via a second cable 51. The electrode segments are arranged on a common support element 43.

The neutral electrode 40 can be applied as an indifferent electrode, particularly in monopolar treatment methods, to a tissue section of a patient and serves finally to conduct away current over a relatively large area. The flat configuration of the electrode segments 41, 42 ensures good current distribution, so that high current peaks do not occur at points across the transition between the tissue and the neutral electrode 40. In this way, burns and similar injuries to the patient can be avoided.

It is advantageous if the neutral electrode 40 can be identified for use thereof. This means that essential parameters of the neutral electrode 40 are identifiable to the surgeon, so that all settings regarding current strength, etc. can be specifically matched on the high-frequency generator 30 to the particular neutral electrode 40. The setting can be carried out by hand, for example, by the surgeon, or the testing device 20 is configured or is connected to a control device 100 such that necessary settings are carried out automatically. Identification of the neutral electrode 40 and the associated matching of setting parameters are especially important, for example, for electrodes to be used with babies and small children. With these electrodes, depending on the identification thereof, a suitable current limit can be set automatically (or by hand).

In this example embodiment, a resistor element 90 is provided for identification of the neutral electrode 40 as an encoding element between the two electrode segments 41, 42. The resistor element 90 has a particular resistance value as the coding which is characteristic of the corresponding neutral electrode 40, so that the precise type of neutral electrode used can be determined. The resistor element 90 is connected between the two conductive electrode segments 41, 42.

In order to detect the resistance value, components of the testing device 20 are connected between the generator 30 and the neutral electrode 40. Aside from the resistor element, the testing device 20 also comprises a direct current source as the test current source 71, a voltage measurement device 70 for indirect detection of the resistance value of the resistor element 90 and an inductor (e.g., a coil as the filter element 80) which enables decoupling of the working current and the test current. These components of the testing device 20 constitute a measurement device 60 and are arranged such that the test current can be conducted via the already existing cables for connecting the neutral electrode 40 to the high-frequency generator 30. The testing device therefore includes the encoding element 90 and the measurement device 60.

The test current can be decoupled as direct current or as low frequency alternating current from the high-frequency working current in that, for example, the coil is provided as a filter, the reactive impedance of which is greater the higher the frequency is.

The direct current is supplied from the direct current source 71; measurement of the resistance value takes place, for example, indirectly via the voltage measurement device 70 with subsequent resistance calculation. It is also possible to use, for example, measuring bridges for resistance determination.

The resistance can be measured using the direct current or a low frequency alternating current (test current) without the test current flowing through the body of the patient. The body of the patient is essentially only capacitively coupled to the electrode. It is not necessary to provide a special connecting cable for signal transmission. A current is thus applied which, for lack of coupling into the body of the patient, cannot be used as a working current and thus enables electrode identification without the need for a special transmission line therefor. A hydrogel 44, 44' applied to the electrodes 41, 42 for contacting the neutral electrode 40 to the tissue 130 of the patient has a chemical composition for this purpose such that said hydrogel represents a high value resistance $R_{Gel}$ and $R'_{Gel}$ for direct current or alternating current at low frequencies (up to ca. 100 Hz). Since the gel has a high resistance in the region of the test current, it is unimportant whether the neutral electrode is placed on the patient, i.e. a low value parallel resistance due to the tissue 130 is present or not. With a type of filter which is in any event present (capacitive coupling of the neutral electrode to the patient) and the use of an "unsuitable" test current, additional cables are not necessary for data transmission in the context of neutral electrode recognition.

As described above, a control device 100 can optionally be provided, by means of which the high-frequency generator 30 is controllable depending on the detected coding value, e.g. depending on the detected resistance value. The high-frequency generator 30 can then be set to a particular current value or a current limit is preset. This is advantageous particularly in the case of neutral electrodes for children, in order to avoid overheating.

The control device 100 can be configured integrally with at least parts of the testing device 20 and the testing device 20 and/or control device 100 can also be configured integrally with the high-frequency generator 30. In one example embodiment, a storage device 110 (which could also be assigned directly to the testing device 20) is also assigned to the control device 100. Thus a particular resistance value can be assigned as the coding for each type of neutral electrode. By means of a table (e.g., type of neutral electrode vs. associated setting parameters) stored in the storage device 110, the high-frequency generator 30, in particular, can be automatically adjusted in the context of an instrument (or electrode)-oriented system configuration to the circumstances at the identified neutral electrode.

Furthermore, an input unit 120 is assigned to the testing device 20 via which input device a user can communicate with the system and, for example, input information which is to be stored.

Figure 2:
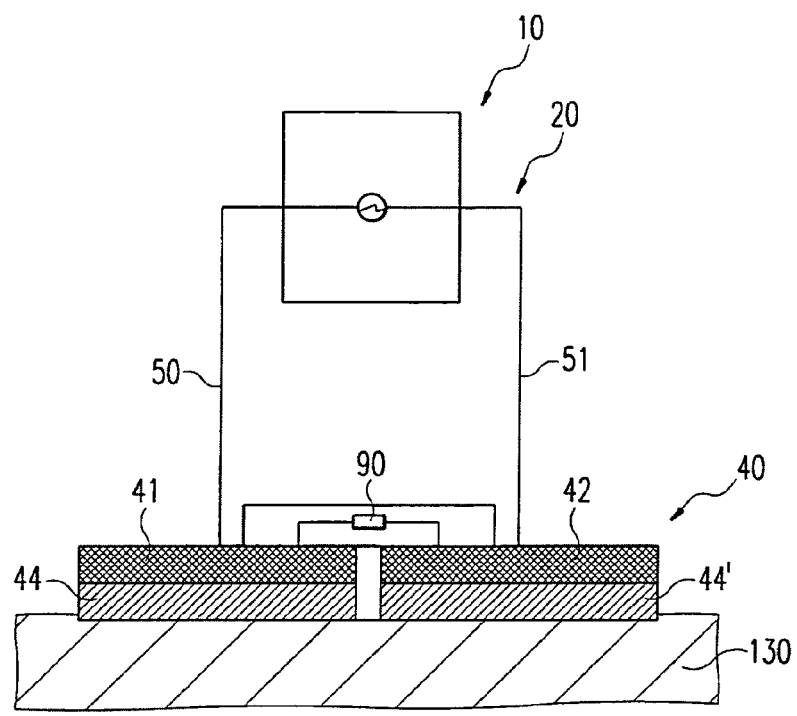
FIG. 2 illustrates a further representation of the embodiment of FIG. 1.
Figure 3:
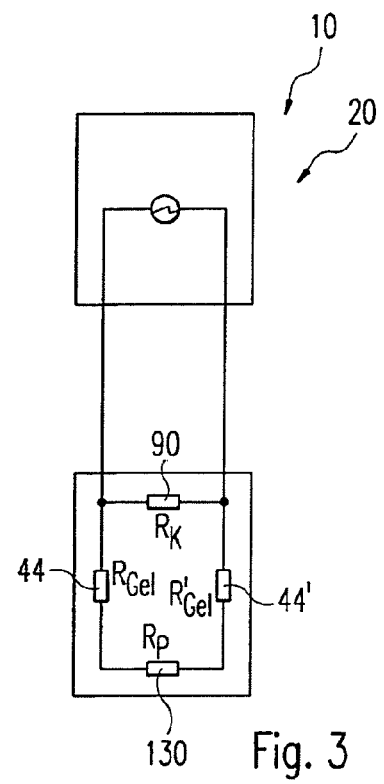
FIG. 3 illustrates a further representation of the embodiment of FIG. 1.

FIGS. 2 and 3 show a different representation of the arrangement shown in FIG. 1. FIG. 2 shows the neutral electrode 40 applied on a tissue section 130 of a patient by means of hydrogel 44, 44'. The two conductive electrode segments 41, 42 are separated from one another by means of a gap. The two electrode segments 41, 42 are connected via the encoding element, the resistor element 90 which has the resistance value that is characteristic of the neutral electrode 40. The test current can be applied via the connecting cables of the electrode segments (cables) 50, 51 for connecting the electrode segments 41, 42 to the high-frequency generator 30 and via the measurement device 60 such that the resistance value can be detected (e.g., measured). The first electrode segment 41 and the second electrode segment 42 lie on top of the gel 44, 44' on the tissue 130 of the patient. The neutral electrode monitoring system, which is integrated, for example, in the high-frequency generator 30 or in a high-frequency surgical device of a high-frequency surgical apparatus 10, is shown in a simplified form. The divided active contact surface (electrode segments 41, 42) is made, for example, from aluminum.

FIG. 3 shows, in the form of an equivalent circuit, the connection between the individual resistors. The encoding element 90, i.e. the resistor element with the resistance $R_K$ is connected in parallel to a patient resistance $R_P$. The two resistors $R_{Gel}$ and $R'_{Gel}$ of the gel layers 44 and 44' under the respective electrode segments behave as if they had high resistance values, as described above.

It is therefore clear that, in order to detect a coding which is characteristic for the neutral electrode, the cables with which the neutral electrode is connected to the high-frequency generator can be used. Using a suitable test current, the parameters of the measuring circuit can be predetermined such that a neutral electrode identification can be carried out with the least possible effort.

It should be pointed out here that all the above described parts and in particular the details illustrated in the drawings are essential for the disclosed embodiments alone and in combination. Adaptations thereof are the common practice of persons skilled in the art.

The invention claimed is:

1. A system comprising:
   a neutral electrode; and
   a high-frequency surgical testing device for testing the neutral electrode during treatment of a biological tissue with a high-frequency current,
   wherein the neutral electrode comprises:
      at least one first electrically conductive electrode segment having a first cable for connecting to a high-frequency generator; and
      a second electrically conductive electrode segment having a second cable for connecting to a high-frequency generator,
      wherein the first and second electrically conductive electrode segments can be brought into contact with biological tissue, and
   wherein the testing device comprises:
      an encoding element; and
      a measurement device,
      wherein the encoding element is directly connected to the first electrode segment and to the second electrode segment and located between the first and second electrode segments of the neutral electrode and includes a coding for describing the type of the neutral electrode, and
      wherein the measurement device further comprises a source for a test current and a filter element, wherein the measurement device detects the coding of the encoding element to identify the type of the neutral electrode, and the filter element enables decoupling of a working current and the test current, and wherein the measurement device is arranged between the first cable and the second cable such that the test current flows through the encoding element via the first cable and the second cable.

2. The high-frequency surgical testing device according to claim 1, wherein the treatment of a biological tissue comprises monopolar coagulation of the biological tissue with the high-frequency current.

3. The high-frequency surgical testing device according to claim 1, wherein the test current is a direct current or a low-frequency alternating current.

4. The high-frequency surgical testing device according to claim 1, wherein the encoding element comprises a resistor element with a resistance value for describing the type of the neutral electrode, wherein the testing device detects the resistance value to identify the type of the neutral electrode.

5. The high-frequency surgical testing device according to claim 4, wherein the resistor element is an ohmic resistor.

6. The high-frequency surgical testing device according to claim 4, wherein the resistor element is a complex resistor with inductive behavior.

7. The high-frequency surgical testing device according to claim 4, wherein the resistor element is a resistor film integrated into the neutral electrode.

8. The high-frequency surgical testing device according to claim 4, wherein the resistor element is a resistor wire integrated into the neutral electrode.

9. The high-frequency surgical testing device according to claim 4, wherein the testing device further comprises a voltage measurement device for measuring a voltage across the resistor element.

10. The high-frequency surgical testing device according to claim 4, wherein the testing device controls settings of a high-frequency generator to which the first and second cables are connected based on the detected resistance value.

11. The high-frequency surgical testing device according to claim 4, wherein the testing device further comprises a control device which controls settings of a high-frequency generator to which the first and second cables are connected depending on the detected resistance value.

12. The high-frequency surgical testing device according to claim 4, wherein the testing device further comprises a storage device, wherein the storage device stores resistance values of different types of neutral electrodes, the stored values being used as comparison values for neutral electrode recognition.

13. The high-frequency surgical testing device according to claim 12, wherein the testing device further comprises an input unit configured such that a user can input the resistance values of different types of neutral electrodes into the storage device.

14. The high-frequency surgical testing device according to claim 1, wherein the testing device further comprises a current measurement device for measuring the test current.

15. The high-frequency surgical testing device according to claim 1, wherein at least a portion of the testing device is integrated into a high-frequency generator to which the first and second cables are connected.

16. The high-frequency surgical testing device according to claim 1, wherein at least a portion of the testing device is integrated into a high-frequency surgical device.

* * * * *

UNITED STATES PATENT AND TRADEMARK OFFICE
CERTIFICATE OF CORRECTION

PATENT NO.        : 8,613,743 B2                                                          Page 1 of 1
APPLICATION NO. : 12/600149
DATED             : December 24, 2013
INVENTOR(S)       : Peter Selig It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 715 days.

Signed and Sealed this
Twenty-second Day of September, 2015

Michelle K. Lee
*Director of the United States Patent and Trademark Office*